(12) United States Patent
Lorraine et al.

(10) Patent No.: US 6,732,587 B2
(45) Date of Patent: May 11, 2004

(54) SYSTEM AND METHOD FOR CLASSIFICATION OF DEFECTS IN A MANUFACTURED OBJECT

(75) Inventors: Peter W. Lorraine, Niskayuna, NY (US); Marc Dubois, Clifton Park, NY (US); Robert J. Filkins, Niskayuna, NY (US); Barbara Venchiarutti, Pordenone (IT)

(73) Assignee: Lockheed Martin Corporation, Bethesda, MD (US)

( * ) Notice: Subject to any disclaimer, the term of this patent is extended or adjusted under 35 U.S.C. 154(b) by 53 days.

(21) Appl. No.: 10/068,255

(22) Filed: Feb. 6, 2002

(65) Prior Publication Data

US 2003/0145655 A1 Aug. 7, 2003

(51) Int. Cl.$^7$ .............................................. G01N 29/04
(52) U.S. Cl. .............................. 73/599; 73/600; 73/602; 73/628
(58) Field of Search ........................ 73/599, 596, 600, 73/602, 606, 627, 628, 643

(56) References Cited

U.S. PATENT DOCUMENTS

| | | | |
|---|---|---|---|
| 4,137,776 A | 2/1979 | Rudis et al. .................... 73/611 |
| 4,205,553 A | 6/1980 | Rudis et al. .................... 73/611 |
| 4,685,334 A | * 8/1987 | Latimer ......................... 73/599 |
| 4,854,173 A | * 8/1989 | Mott et al. ..................... 73/600 |
| 4,898,034 A | 2/1990 | Kupperman et al. .......... 73/644 |
| 5,095,744 A | 3/1992 | Macecek et al. ............... 73/146 |
| 5,168,469 A | * 12/1992 | Liberto et al. ................. 367/11 |
| 5,417,114 A | 5/1995 | Wadaka et al. ................ 73/602 |
| 5,431,053 A | 7/1995 | Fink .............................. 73/602 |
| 5,439,157 A | * 8/1995 | Geier et al. ..................... 228/9 |
| 5,442,284 A | 8/1995 | Kolditz ........................ 324/220 |
| 5,589,635 A | 12/1996 | Baudrillard et al. ........... 73/600 |
| 5,628,319 A | 5/1997 | Koch et al. ............. 128/660.01 |
| 5,637,799 A | 6/1997 | Heyman et al. ............... 73/600 |
| 5,661,243 A | 8/1997 | Bryan et al. ................... 73/632 |
| 5,841,031 A | 11/1998 | Chung ........................... 73/583 |
| 5,894,092 A | 4/1999 | Lindgren et al. .............. 73/598 |
| 5,982,482 A | 11/1999 | Nelson et al. ............ 356/237.1 |
| 5,996,413 A | 12/1999 | Iyer et al. ...................... 73/592 |
| 6,041,020 A | * 3/2000 | Caron et al. .................. 367/149 |
| 6,065,348 A | 5/2000 | Burnett ......................... 73/801 |

(List continued on next page.)

FOREIGN PATENT DOCUMENTS

| | | |
|---|---|---|
| EP | 0076168 A2 | 4/1985 |
| EP | 0193924 A2 | 12/1987 |
| EP | 0352117 A1 | 1/1990 |
| EP | 0565570 A1 | 12/1992 |
| EP | 0614084 A1 | 9/1994 |

OTHER PUBLICATIONS

US 2003/0033878A1 Method and apparatus to conduct ultrasonic flaw detection for multilayered struicture.*

*Primary Examiner*—Hezron Williams
*Assistant Examiner*—Jacques Saint-Surin
(74) *Attorney, Agent, or Firm*—Koestner Bertani, LLP

(57) ABSTRACT

Ultrasonic testing techniques may involve the measurement of ultrasonic waves from the tested part. These waves may reflect from surfaces of various layers within the part. Further, these waves may reflect from faults, defects, voids, fractures, and others. As such, the measured ultrasonic wave is a complex mix of these reflections. One method for detecting flaws, defects, and others may be to express the signal in terms of a set of basis functions. These functions may be summed to produce the measured signal. Further, basis functions may be chosen such that a select set of the basis functions characterize the fault and/or defect. In one exemplary embodiment, the coefficients associated with the basis function may be non-zero when a defect is present. As such, a defect may be detected quickly and automatically.

25 Claims, 17 Drawing Sheets

U.S. PATENT DOCUMENTS

| | | | |
|---|---|---|---|
| 6,125,704 A | 10/2000 | Wang | 73/602 |
| 6,138,514 A * | 10/2000 | Iwamoto et al. | 73/622 |
| 6,182,512 B1 * | 2/2001 | Lorraine | 73/655 |
| 6,269,699 B1 * | 8/2001 | Gilman et al. | 73/601 |
| 6,276,209 B1 | 8/2001 | Schafer et al. | 73/597 |
| 6,302,314 B1 * | 10/2001 | Horio et al. | 228/103 |
| 6,324,912 B1 * | 12/2001 | Wooh | 73/629 |
| 6,360,609 B1 * | 3/2002 | Wooh | 73/602 |
| 6,487,910 B1 * | 12/2002 | Leybovich | 73/620 |
| 6,532,820 B1 * | 3/2003 | Fleming et al. | 73/627 |

* cited by examiner

SYSTEM AND METHOD FOR CLASSIFICATION OF DEFECTS IN A MANUFACTURED OBJECT

BACKGROUND OF THE INVENTION

The present invention generally relates to a system and method for interpreting sonic data. In particular, the present invention relates to a system and method for detecting flaws and/or defects in parts through analysis of ultrasonic data. The present invention relates generally to the nondestructive evaluation of materials, and more particularly to laser ultrasound inspection of engineering materials with ultrasonic bulk, surface, and Lamb waves.

DESCRIPTION OF PRIOR ART

Measurement of ultrasound is commonly performed to characterize materials. This includes measuring and detecting structures, and can be implemented to find defects or flaws within the parts or contained in the materials making up the parts.

Within many industries, inspection of engineering materials has extreme importance in assuring continued performance of structures. In other systems, parts or components need to be evaluated for defects or flaws. Many times these parts may be highly sensitive pieces made in complex engineered fashion and made up of complex materials.

Generated sonic waves propagate through an article. Defects in the part may reflect the waves or change other physical parameters associated with the wave. These sonic waves may be detected, and stored for later analysis.

These waveforms may be converted into a visual image to aid in diagnosing problems. Many times, in a typical system, and arrival of the sonic energy may be used to determine visually where a defect is, and possibly what type of defect is present.

However, this typical analysis of the collected waves usually only indicates a presence of a problem, and may not completely diagnose or locate a particular defect in the part or underlying material. Thus, while the conventional analysis may indicate the presence of a defect or flaw, it may not adequately describe the type and/or physical location of the defect or flaw.

This problem is exacerbated when dealing with composite parts. The interlocking or coupled relationship of various layers of materials, or type of construction gives rise to multiple complex echoes. Thus, in these systems, the echo waveform may not be easily used for visualization or interpretation.

As such, many typical sonic detection systems suffer from deficiencies in providing accurate indications of defects. Many other problems and disadvantages of the prior art will become apparent to one skilled in the art after comparing such prior art with the present invention as described herein.

SUMMARY OF THE INVENTION

Various aspects of the invention may be found in a method for detecting more and more defects in manufactured object. The invention converts complex measured ultrasonic waveforms into basis functions indicative of any defects within that part. First, a series of reference waveforms corresponding to the ideal part and or to flaws of various types at various places in depths within the part are generated. These reference waveforms form a series of basis functions that may be helpful in describing any observed waveform. Since a measured waveform may be represented in terms of an inner sum of these basis functions and the amplitudes of each basis function that correspond to a presence of that particular type of defect, the presence of the basis function corresponding to a particular type of defect indicates that in the particular type of defect is present.

In typical measurement systems, a series of waveforms may be generated from the part. Even in a simple layered structure, a complex series of echoes is generated in an ideal part. Additionally, the presence of any defects will alter the waveform within the part. However, due to the complex nature of the sonic characteristics of the part, defect location by echo timing is problematic.

However, in the present system, the waveforms for particular defects at particular location(s) may be stored as waveforms, and these may be added in combination with the ideal waveform to produce a reference waveform. The combination of a reference ideal waveform for the part, and the basis functions for defects are compared against the received waveform for the part. The presence of any of the basis functions for a corresponding defect thus indicates the location and type of defect present in the part.

In this way, a defect in an interface is represented by the amplitude corresponding to that sort of defect, rather than as a series of complex echoes. This technique may be applied in a variety of situations. This includes simple parts where multiple echoes are generated from a single flaw, for example, a reverberation against either a front or back wall, or for separation and identification of flaws near the front or rear surfaces of the part.

The various comparison waveforms or representations of such waveforms may be generated in several ways. For example, the basis functions may be derived through a computational model, or they may be derived through experimental measurements of reference parts. In the case of basis functions referring to defects, the reference parts were contained a known defect. Thus the type and parameters of the waveforms generated by the specific defect may be groomed from such experimental measurement.

Other aspects of the invention include describing the defective structures by using the amplitudes of these basis functions to draw images. When the presence of the basis function indicating a specific flaw or defect type is determined, an image of the part or location may be generated. A simple graph such as a graph of amplitude versus location may indicate the specific point where a flaw is located. Other imaging schemes may include B-scans and C-scans where both B and C are capitalized. In these B-scans or C-scans, the parameter viewed would be the amplitude of various basis functions. Thus, the presence of an amplitude for a basis function at a particular location in a B-scan or C-scan would indicate the presence of the particular type of defect associated with the basis function at the point on the object.

In another aspect of the invention, the detection of flaws or defects is improved even in the presence of noise. Further descriptions of how this method aids in the detection of such defects or flaws in the presence of noise is described in detail later in this application.

Other aspects, advantages and novel features of the present invention will become apparent from the detailed description of the invention when considered in conjunction with the accompanying drawings.

DETAILED DESCRIPTION

Figure 1:
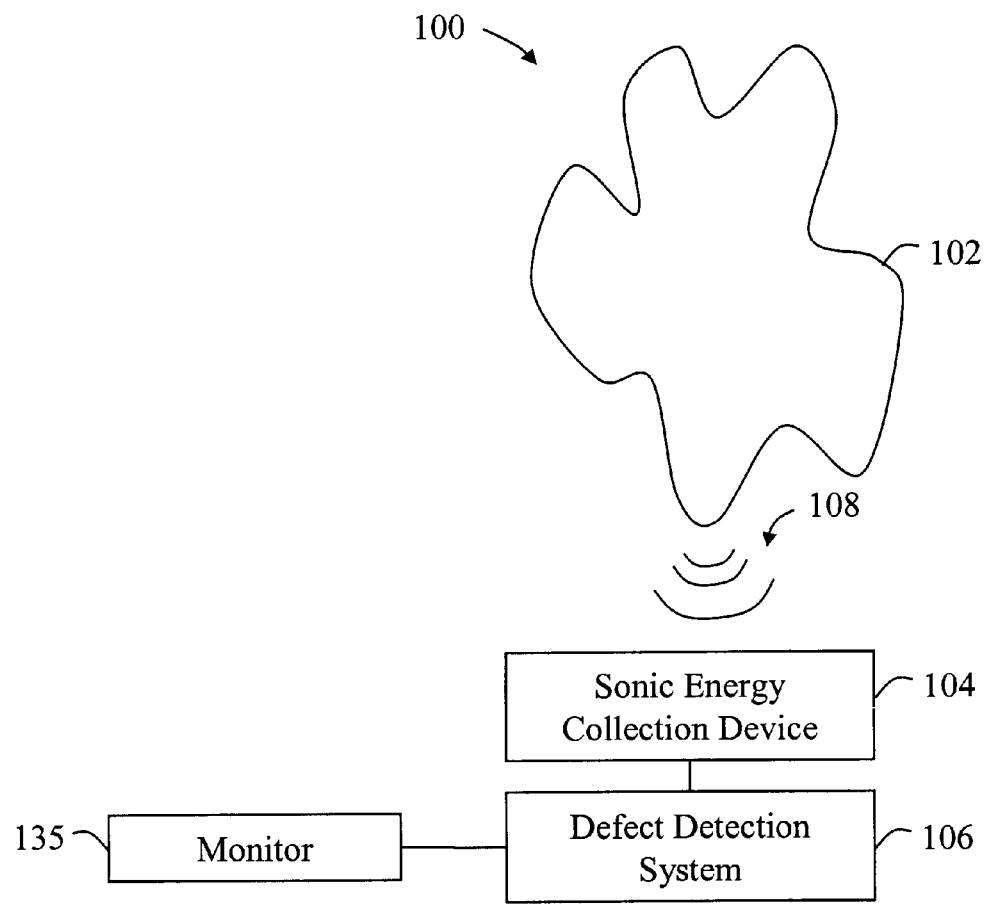
FIG. 1 is a schematic block diagram of a system that diagnoses, locates, and classifies defects in parts using sonic waves, according to the invention.

FIG. 1 is a schematic block diagram of a system that diagnoses, locates, and classifies defects in parts using sonic waves, according to the invention. A sonic testing system 100 contains a sonic wave generator. The sonic wave is generated in a number of ways, including by a laser that directs coherent electromagnetic radiation to a tested part 102, a piezoelectric transducer attached to the part, or an electromagnetic transducer (EMAT) Typically this sonic energy is ultrasound energy.

The sonic energy propagates through the part 102, and is detected in a sonic energy collection device 104. The sonic energy may also be detected in a number of ways, including laser interferometer techniques, piezoelectric transducers attached to the part, and EMAT systems. Or a gas buffer measurement technique in which the sonic energy passes to a gaseous medium, and pressure in this medium is measured through such techniques as a laser.

In some cases, a defect creates reflections in the medium making up the part. Or, the defect may change velocity parameters, attenuation parameters, or other characteristics of the sonic energy. In any case, the sonic energies are transformed in some manner by a defect. The defect may then be identified and/or located through the detection of anomalous sonic signals.

The collected sonic energies are converted to an electric signal and stored in some format. In this example, the energy collection device is tethered to a computer. The energy collection device and/or the computer can convert the collected signals to an appropriate format, and store them for later analysis.

In an exemplary embodiment of the invention, the stored signal is compared to a reference waveform corresponding to an ideal part. Additionally, basis waveforms for various kinds of defects are also stored. The basis waveforms correspond to the waveforms generated by particular flaws, and can include such parameters as a particular flaw at a particular depth.

The measured waveform is then represented in terms of the ideal waveform and or the basis waveforms. The measured waveform may be thought of as a linear sum of the ideal part reference waveform and any basis waveforms for a particular defect at a particular location.

In algebraic terms, a measured waveform Y(t) may be signified as:

$$Y(t)=X_1 bf_1(t)+X_2 bf_2(t)+X_3 bf_3(t)+ \ldots X_m bf_m(t). \quad \text{(Eqn 1)}$$

where the m $X_i$ are the amplitudes of the m $bf_i$ that are basis functions as described previously. Thus, in the present invention, the measured wave may be compared against linear combinations of the ideal wave and any basis functions.

In the measurement system, a defect detection system 106 detects defects in the part 102. This is accomplished by comparing the received waveform with the ideal waveform and such basis functions. The defect detection system may operate in real time, or it may operate on previously stored data. In any case, the defect detection system 106 compares the observed wave with a combination of basis functions describing the response of the part and the response associated with any defects.

For discretely time sampled waveform data, the matrix notation of the discrete time sampled measured wave function y may be delineated as:

$$\begin{pmatrix} y_o \\ \vdots \\ y_n \end{pmatrix} = \begin{pmatrix} bf_{00} & \cdots & bf_{mo} \\ \vdots & \ddots & \vdots \\ bf_{om} & \cdots & bf_{mn} \end{pmatrix} \begin{pmatrix} x_o \\ \vdots \\ x_m \end{pmatrix}$$

In this sense, the vector Y is the time sampled waveform data, the matrix $\underline{\underline{BF}}$ is a matrix of appropriate basis functions, and the coefficient vector X contains the amplitudes associated with the basis functions described in the matrix $\underline{\underline{BF}}$. Thus, when a defect of a particular type is present, the appropriate coefficient will be non-zero.

A monitor 135, or other visualization method, is available to view the data. In one embodiment, the amplitude of a coefficient is mapped to a color scheme at the appropriate location. Thus, a color-generated map may be generated indicating the location of where the coefficient is higher and lower, allowing an observer to decide where a particular defect is in the part or materials making up the part.

It should be noted that the implementation of the wave comparison is easily implemented in a digital computer. In this manner, the basis functions may be added easily as they are determined.

The basis functions may be determined in a variety of ways. They may be derived by empirically testing parts and deriving the defect functions based on the results. Or, the basis functions may be determined though computer modeling techniques.

In an exemplary embodiment, the characteristic amplitudes of the various basis functions may be directly derived form the observed data itself. From Eqn. 1, the equation for the real time digitally sampled response of the part, we can show that:

$$(\underline{bf}^t\underline{bf})^{-1}\underline{bf}^t\underline{y}=(\underline{bf}^t\underline{bf})^{-1}\underline{bf}^t\underline{bf}\underline{x}=\underline{x}$$

where bf is the basis function matrix, the superscript t denotes the transpose of the matrix, the superscript −1 denotes the inverse of the matrix, y is the observed results, and x is the vector of amplitudes for the basis functions making up the signal. Thus, the entire range of amplitudes for the basis functions can be determined for a defect space. A non-zero amplitude indicates that a particular type of defect is present.

The amplitude vector may also be a function of position. Thus, the same state space analysis may be employed not just for the presence of some specific defect, but may occur for determining the specific location of it as well. In this case, if the amplitude is viewed on a scale of position, the specific point where the defect occurs may be viewed, as the amplitude will rise to a non-zero value on a localized basis.

The amplitude vector may be plotted using B-scans or C-scans of the part or object. Where particular amplitude goes from zero to non-zero, this indicates the presence of a particular defect or flaw in the measured object at that point. Thus, the inherent properties of the object and the specific defects are used to identify and/or locate with particularity these problems. Thus, the object may be graphically reproduced in several dimensions with the amplitude characteristics of the defects.

Figure 2:
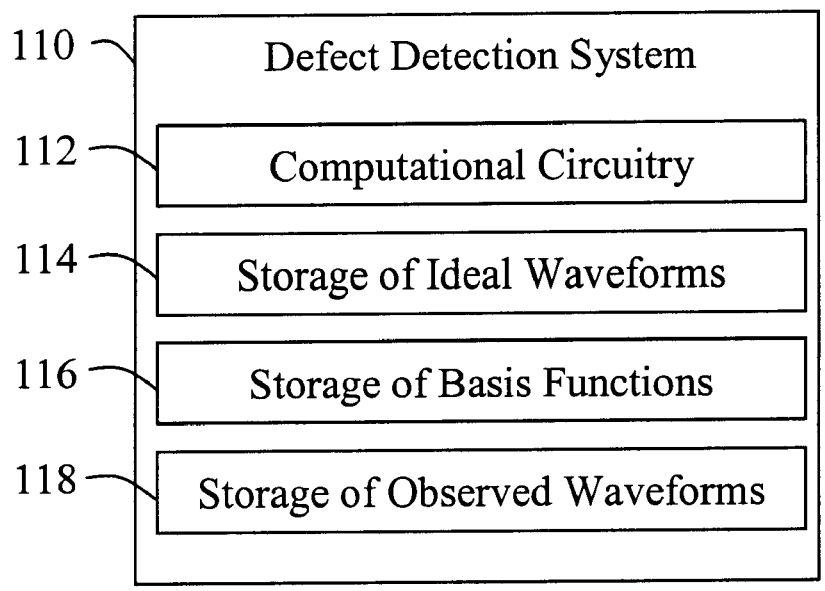
FIG. 2 is block diagram of an exemplary defect detection system of FIG. 1.

FIG. 2 is block diagram of an exemplary defect detection system of FIG. 1. The defect detection system 110 contains storage of ideal waveforms, storage of basis waveforms, storage of observed waveforms, and computational circuitry. This circuitry takes the ideal waveforms and basis waveforms, and compares them to the observed waveform in the computational circuitry. It should be noted that the components of the defect detection circuitry may exist all together in a stand-alone component, or may exist in whole or in part in the various components discussed in reference to FIG. 1.

FIGS. 3–6 are time domain wave diagrams detailing how the system of FIG. 1 might work. In these figures, an observed waveform is compared to a linear combination of basis function 1, basis function 2, and/or an idealized waveform.

Figure 3:
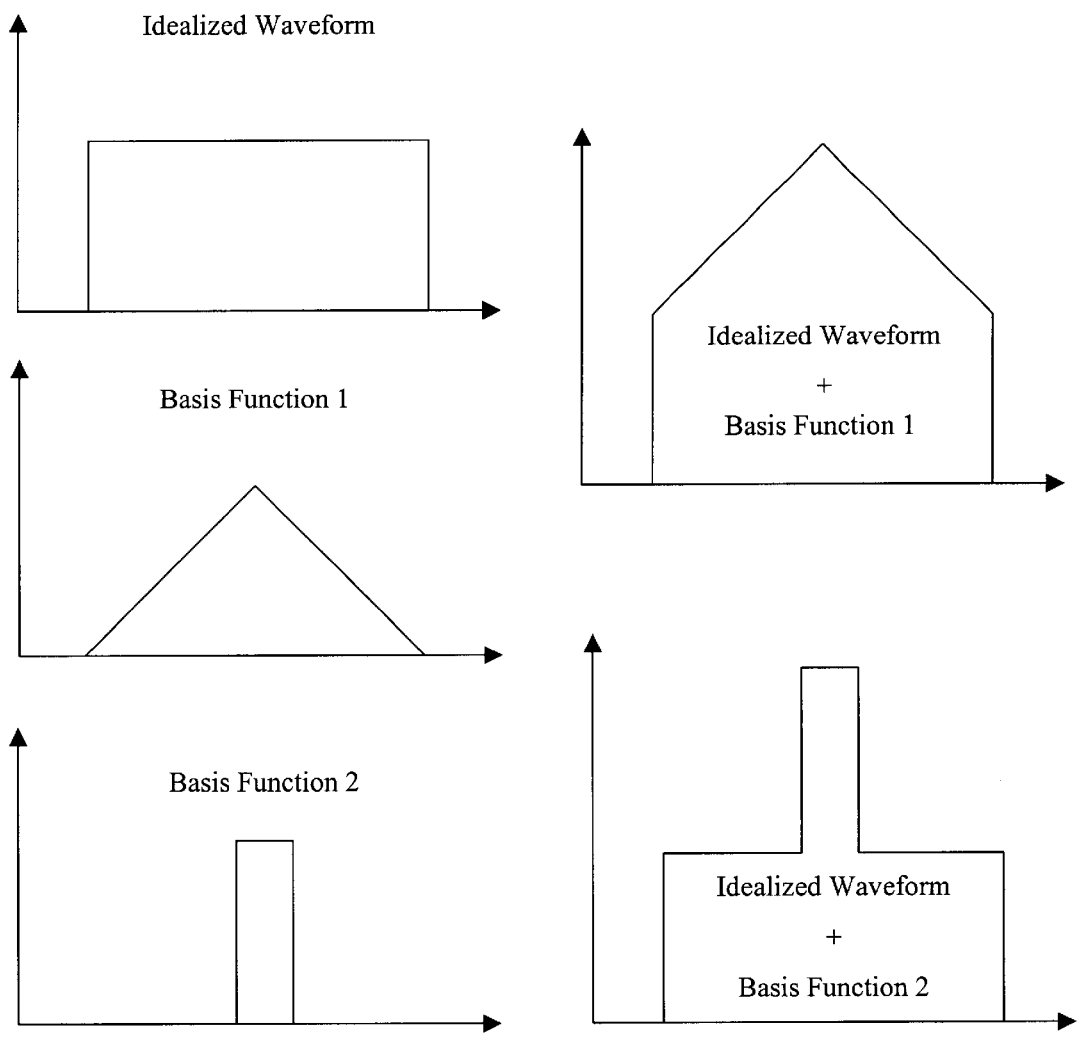
FIGS. 3–6 are time domain wave diagrams detailing how the system of FIG. 1 might work.
Figure 4:
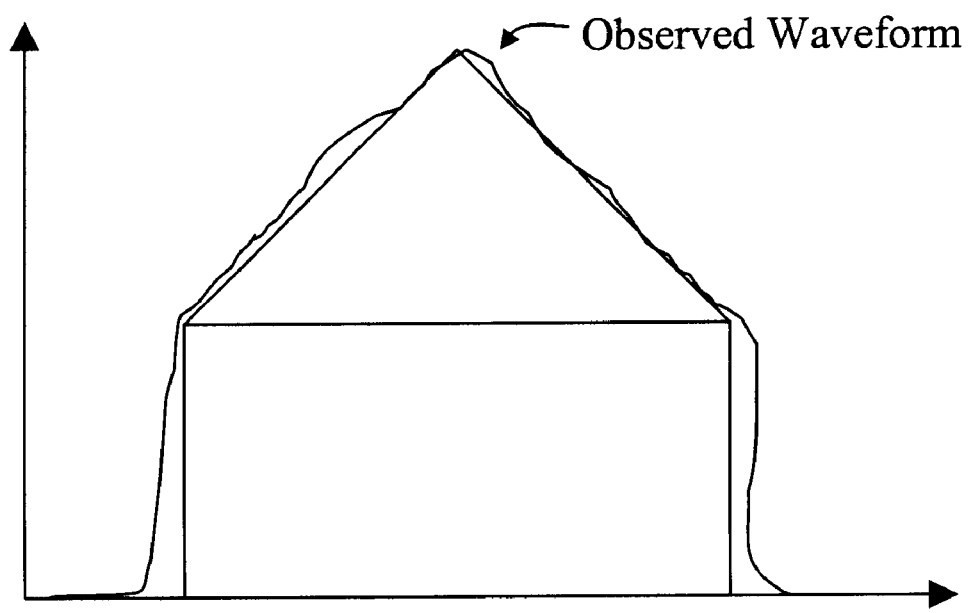

In FIG. 3, the linear combinations of the idealized waveform and the basis functions are performed. FIG. 4 shows the comparison of the linear combinations with an observed waveform. The observed waveform corresponds directly with the waveform indicative of the defect associated with the basis function 1, and as such, a report may be generated that shows the presence of the defect associated with the basis function 1.

Figure 5:
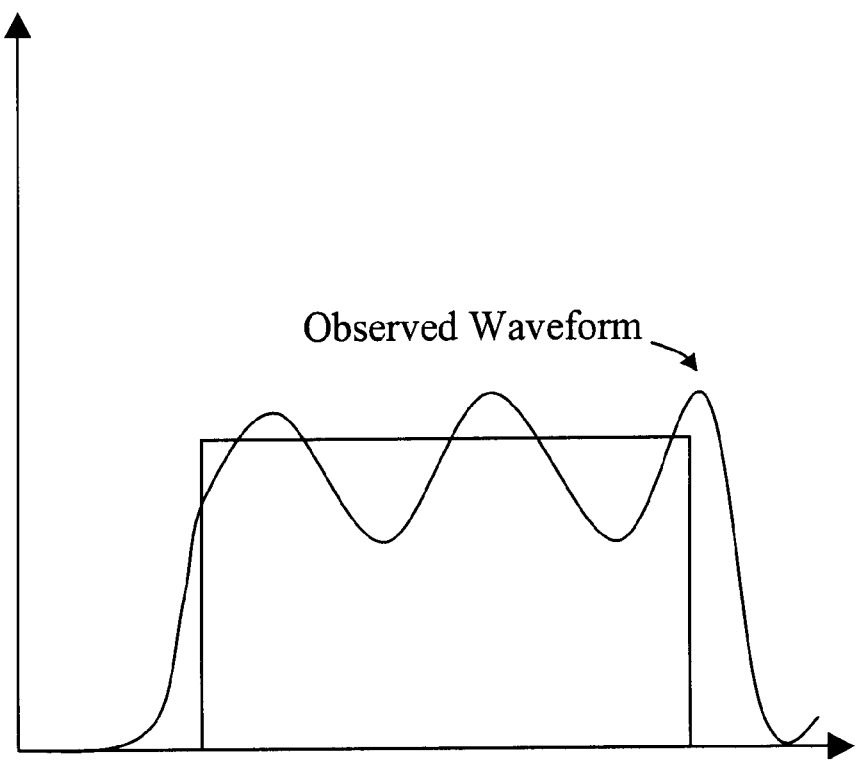

FIG. 5 shows a situation where the observed waveform does not correlate with any combination of the idealized waveform and basis functions. This indicates the possible presence of a defect, but the defects associated with the basis functions 1 and 2 may be discounted.

Figure 6:
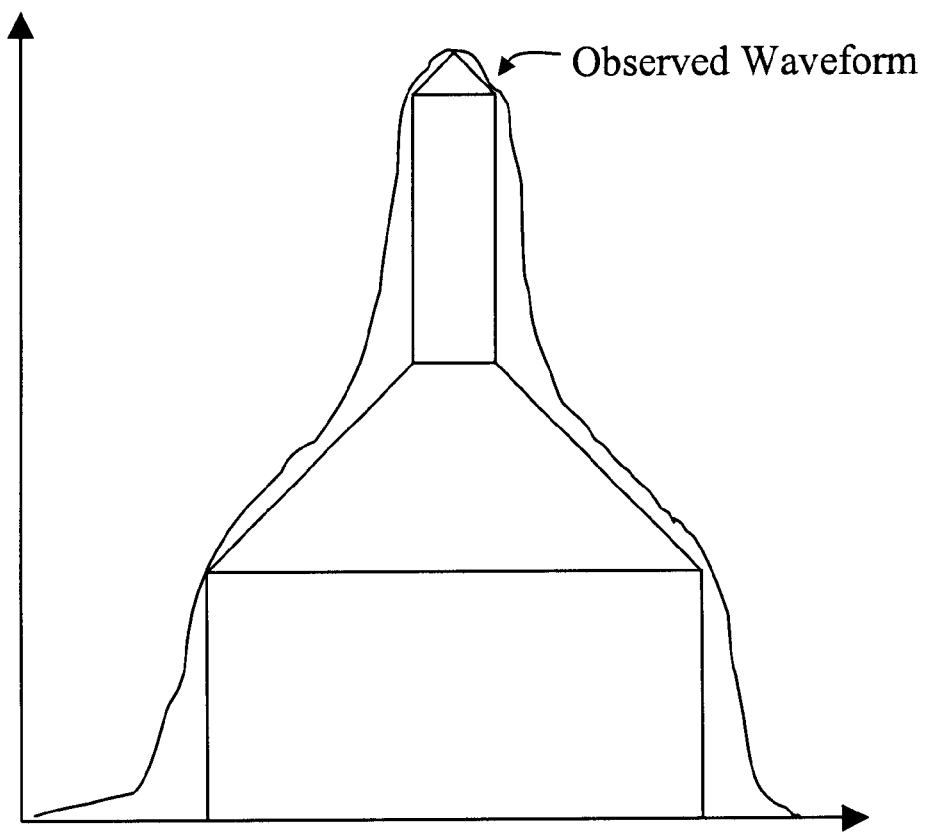

FIG. 6 shows a situation that corresponds with the presence of both basis functions. This would tend to indicate that the defects associated with the basis functions 1 and 2 are both present.

Figure 7:
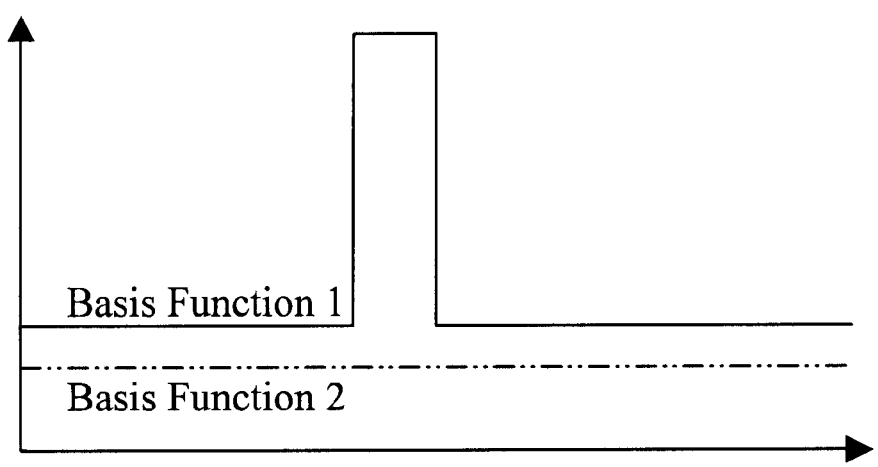
FIGS. 7, 8, and 9 are plots of basis function amplitudes as a function of position where the cases of FIGS. 4, 5, and 6, are illustrated respectively.
Figure 8:
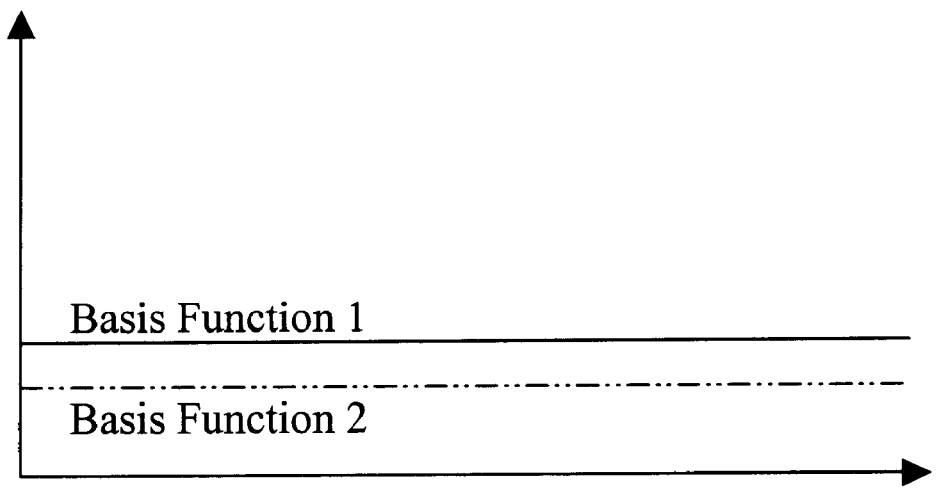
Figure 9:
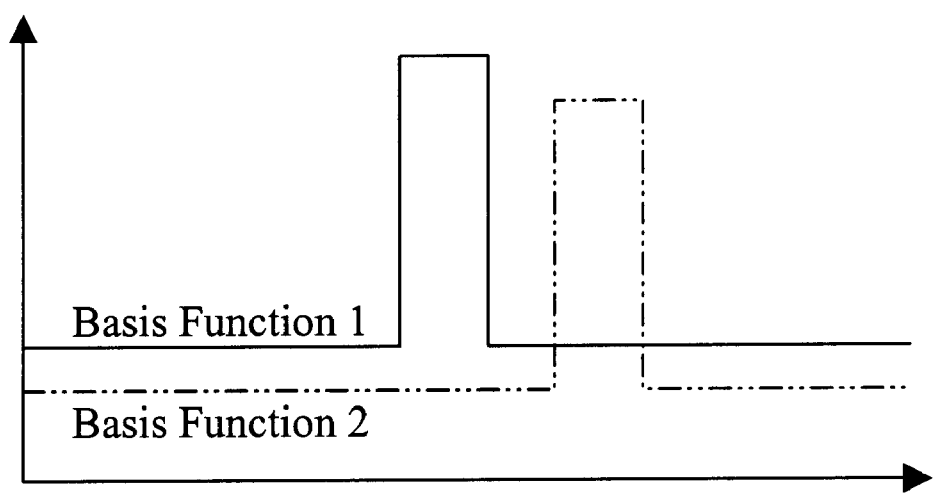

FIGS. 7, 8, and 9 are plots of the basis function amplitudes as a function of position for FIGS. 4, 5, and 6, respectively. FIG. 7 shows a non-zero value in the amplitude of basis function 1 at the point where the defect occurs. Thus, the defect associated with basis function 1 is present at that point. FIG. 8 shows no change in the amplitude of either of the basis functions. Thus, neither of the defects is present in the object at any measured point, although some other defect not described by the basis functions may very well exist. FIG. 9 shows a change in the amplitude of basis function 1 at the points where the defects occur. It also shows a change in the amplitude of basis function 2 at the point where the second defect occurs. Thus, both defects associated with basis functions 1 and 2 are present in the object at some of the measurement points.

The amplitude viewing may also localize defects much more efficiently when noise is present in the system. In this case, the analysis of a part may be made easier in the presence of noise.

Figure 10:
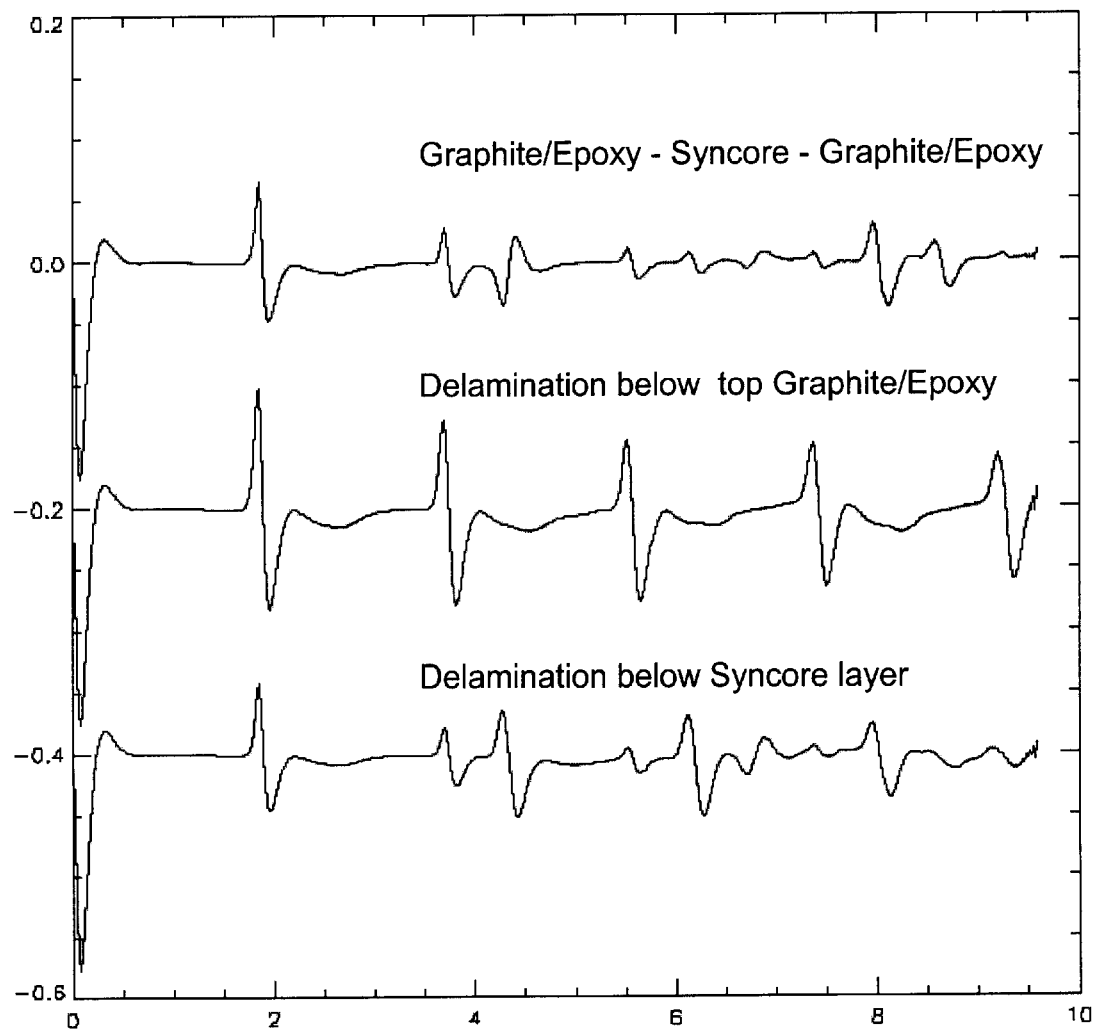
FIG. 10 is a time domain representation of a set of waveforms from a target measurement.

FIG. 10 is a time domain representation of a set of waveforms from a target measurement. The waveforms indicate that the determination of a defect by reflection echo timing is problematic. Additionally, for multi-material layered objects, the echo interactions between the layers may make the problem even more difficult.

Figure 11:
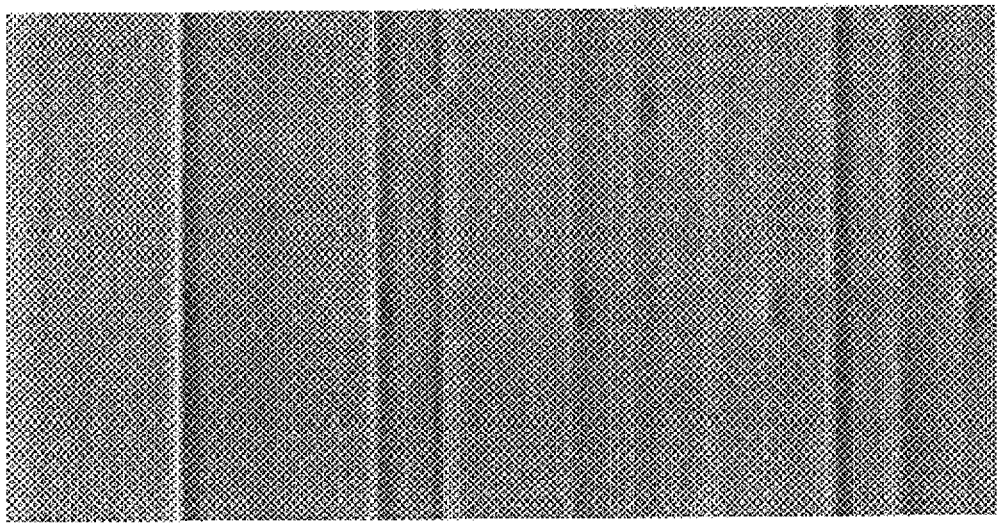
FIG. 11 is a B-scan image corresponding to the noiseless waveforms of FIG. 10, indicating the presence of multiple defects in its construction and/or make up.
Figure 12:
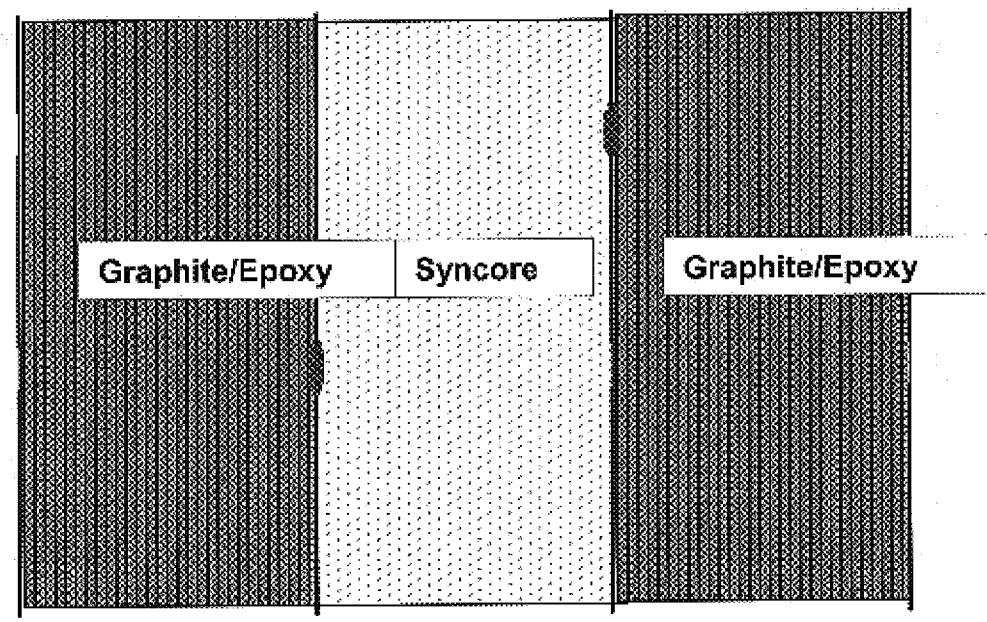
FIG. 12a shows the location of simulated defects in a part as indicated in FIG. 11.
FIG. 12b depicts plots of basis function amplitudes versus position for the waveforms depicted in FIG. 10.
Figure 12:
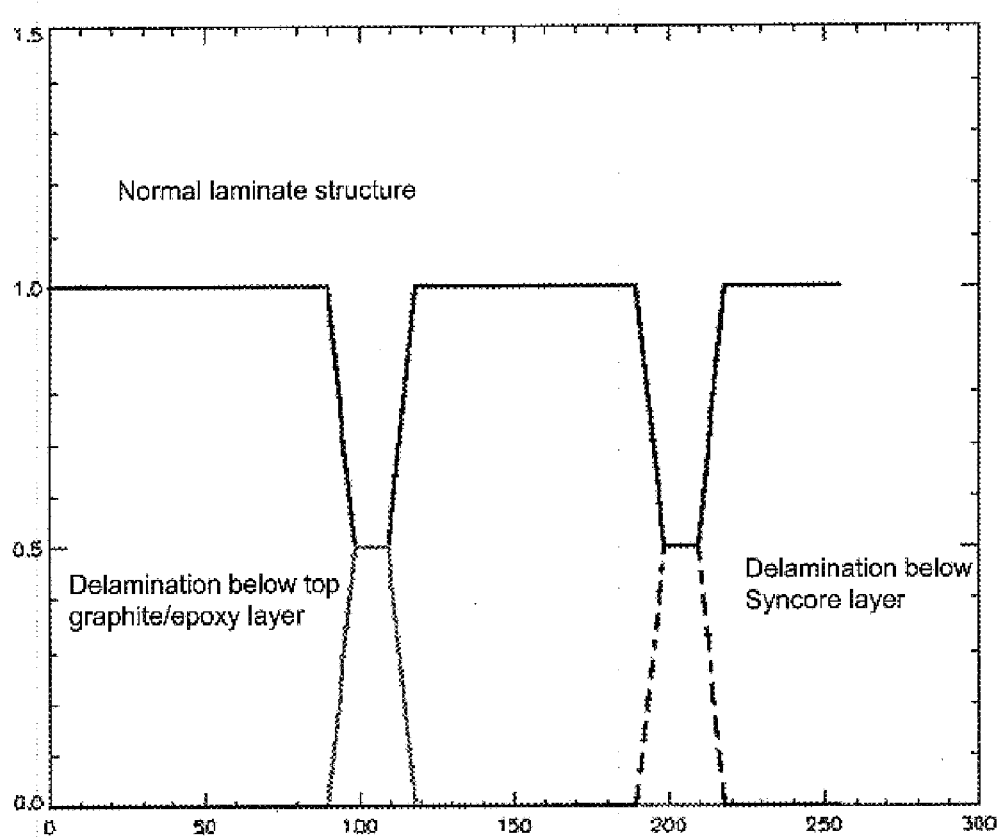

FIG. 11 is a B-scan image corresponding to the noiseless waveforms of FIG. 10, indicating the presence of multiple defects in its construction and/or make up. FIG. 12a shows the location of simulated defects in a part as indicated in FIG. 11. FIG. 12b depicts plots of basis function amplitudes versus position for the waveforms depicted in FIG. 10.

Figure 13:
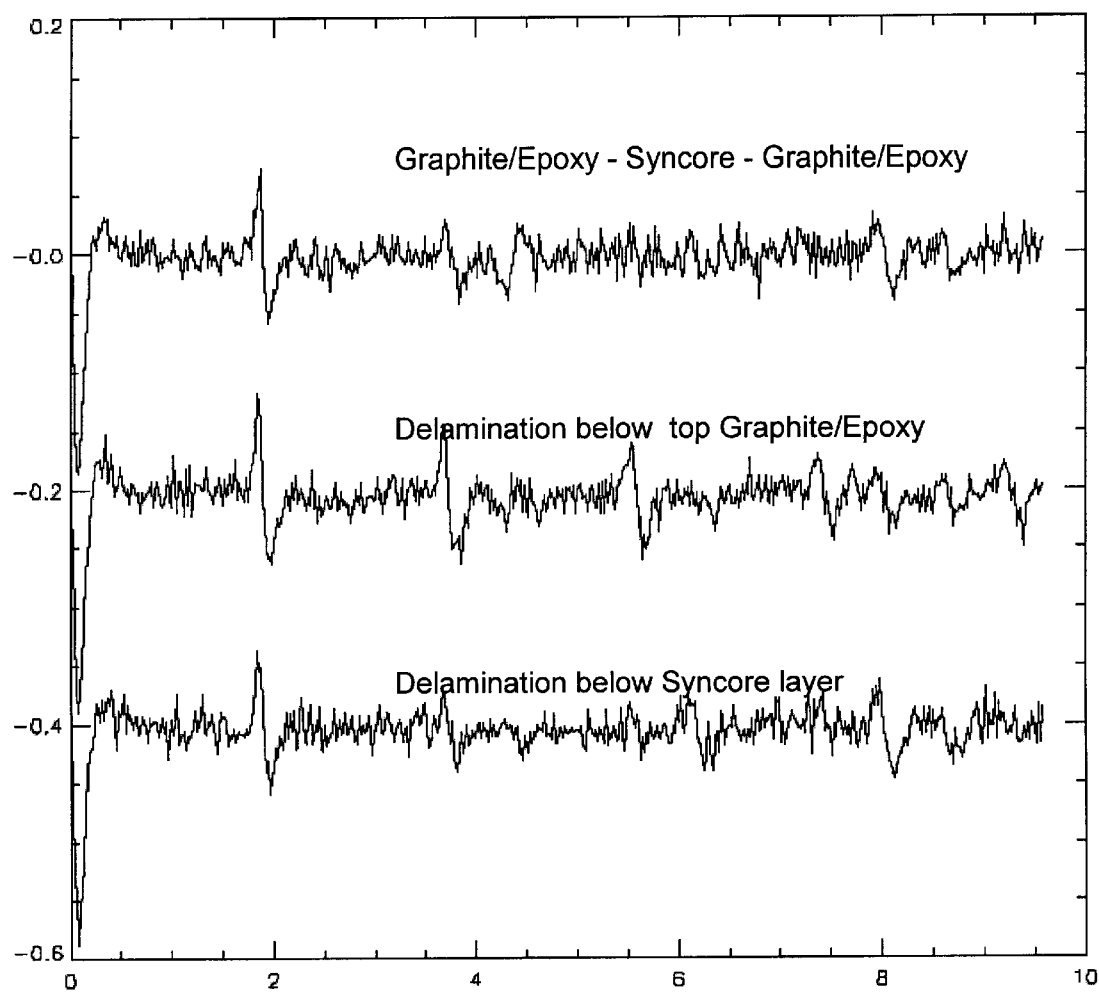
FIG. 13 is a time domain representation of the waveforms of FIG. 10, but having noise present.

FIG. 13 is a time domain representation of the waveforms of FIG. 10, but having noise present. The amplitude of the noise is comparable to the signal amplitude. The ability to detect the reflection echoes is significantly reduced in this, and the signal to noise ratio (SNR) is low.

Figure 14:
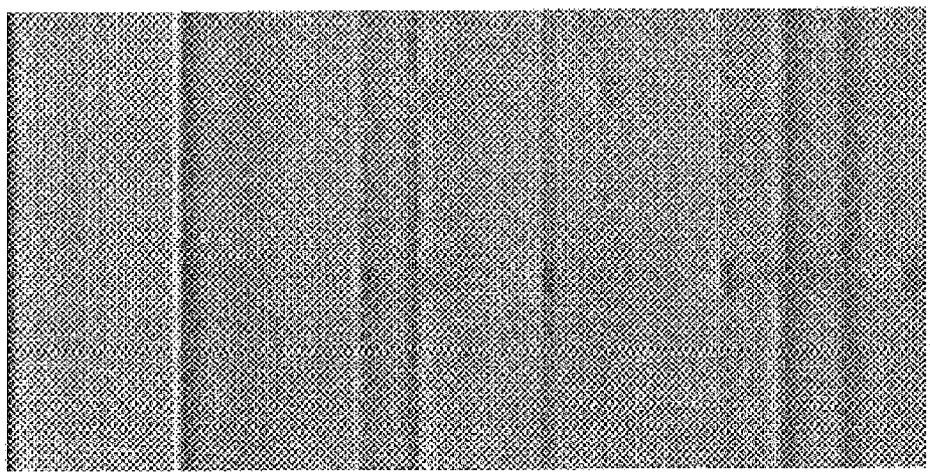
FIG. 14 is a corresponding B-scan of the waveform of FIG. 13.

FIG. 14 is a corresponding B-scan of the waveforms of FIG. 13. Note that the defects are harder to read the due to the added noise.

Figure 15:
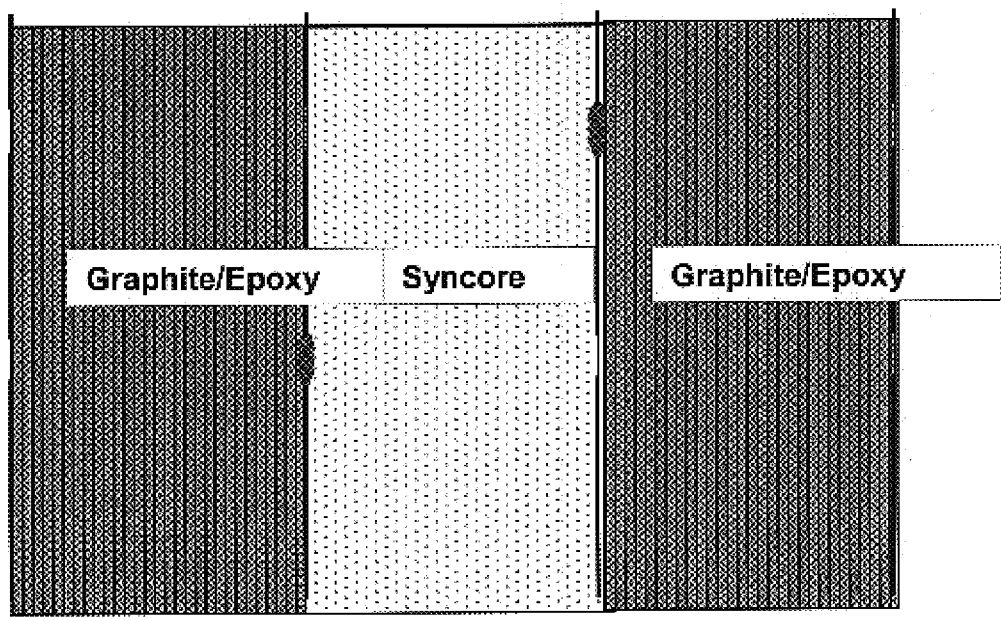
FIG. 15a shows the location of simulated defects in a part as indicated in FIG. 14.
FIG. 15b depicts plots of basis function amplitudes versus position for the waveforms depicted in FIG. 13.
Figure 15:
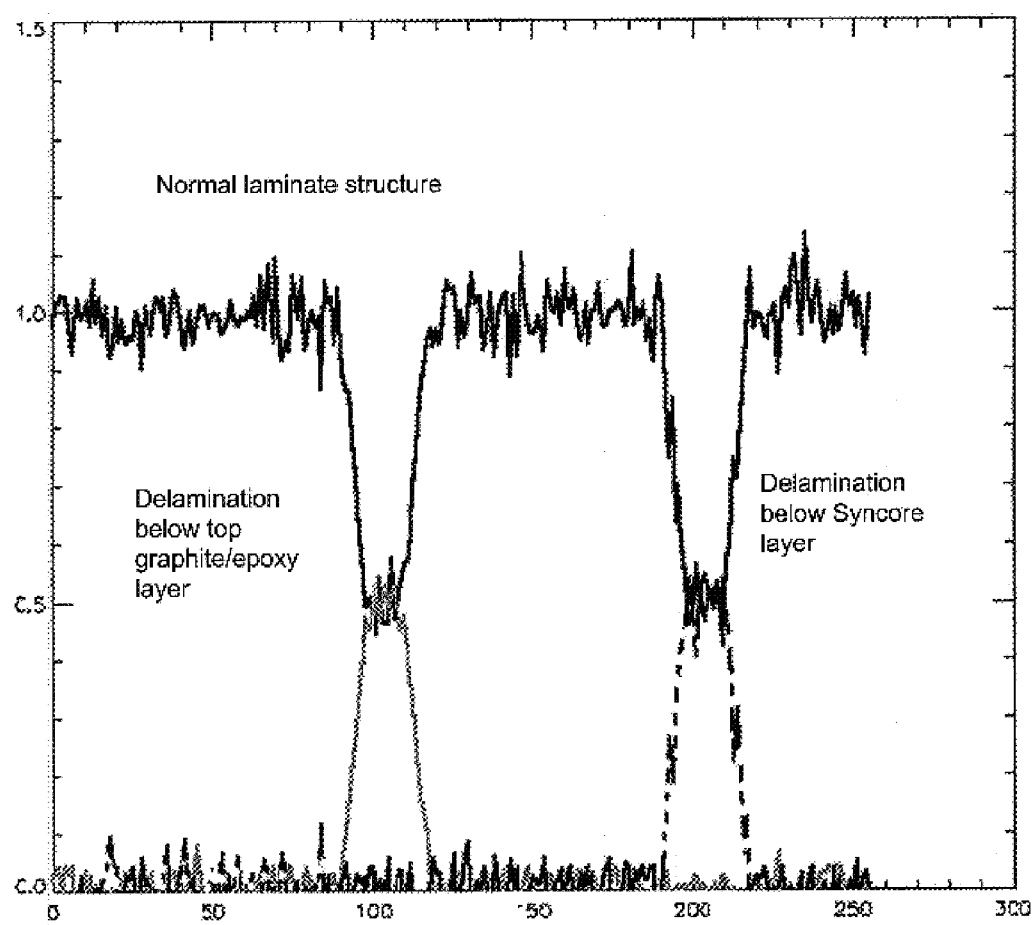

FIG. 15a shows the location of simulated defects in a part as indicated in FIG. 14. FIG. 15b depicts plots of basis function amplitudes versus position for the waveforms depicted in FIG. 13. Note that the amplitude information is extremely easy to read and to indicate the presence of defects, even in the presence of added noise. As such, the SNR for this case is much higher than that of the raw data. This tends to point out and to locate defects with greater precision.

The techniques may be extended to include frequency and phase domain descriptions of the waveforms. This is an alternative to the amplitude and time domain descriptions used in the previous description.

As such, a system and method for determining flaws in an object through the application of defect basis functions are described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed is:

1. A method to detect defects in a manufactured part using ultrasonic waves ultrasonic waves, comprising:
   inducing ultrasonic waves into the manufactured part;
   measuring reflected ultrasonic waves, wherein the reflected ultrasonic waves comprise reflections of the induced ultrasonic waves;
   expressing the measured reflected ultrasonic waves as a sum of a set of basis functions wherein each basis function has a coefficient; and
   determining the presence of a defect when a coefficient for a defect basis function is non-zero.

2. The method of claim 1, wherein the set of basis functions comprise:
   basis functions for structures within the manufactured part; and
   basis functions for defects within the manufactured part.

3. The method of claim 1, wherein at least one basis function is based on modeled results.

4. The method of claim 1, wherein at least one basis function corresponds to a particular flaw.

5. The method of claim 1, further comprising determining the coefficient for each basis function.

6. The method of claim 1, further comprising displaying a graph associated with the manufactured part, the graph indicative of the presence of the one or more basis functions.

7. The method of claim 6, further comprising generating a B-scan image.

8. The method of claim 6, further comprising generating a C-scan image.

9. A system for detecting flaws in a manufactured object, the system comprising:

a device to generate ultrasonic waves in the manufactured object;

a detection laser, scattered by the ultrasonic waves at the surface of the manufactured object;

an optical system that collects scattered laser energy to produce an output representative of the acoustic waves within the manufactured object; and a processor:
to transform the output representative of the acoustic waves within the manufactured object to a sum of individual wave functions, wherein each wave function has a coefficient;
to identify flaws within the manufactured object as having non-zero coefficients associated with wave functions representing the flaws.

10. The system of claim 9, wherein the coefficient have both an amplitude and a basis function.

11. The system of claim 9, wherein the wave function representing a flaw has:

an amplitude corresponding to a size of the flaw; and a basis function corresponding to a type of the flaw.

12. The system of claim 9 wherein the manufactured objects comprises a composite material.

13. The system of claim 9, further comprising a graphical user interface to present a representation of the presence of a flaw.

14. The system of claim 13, wherein the representation is a B-scan image.

15. The system of claim 13, wherein the representation is a C-scan image.

16. An ultrasound system to inspect materials, comprising:

a generation device to generate ultrasonic waves in the materials;

a detection device to measure ultrasonic waves at the surface of the material and to produce an output representative of the ultrasonic waves within the material; and a processor:
to transform the output representative of the acoustic waves within the material to a sum of individual wave functions, wherein each wave function has a coefficient;
to identify flaws within the material as having non-zero coefficients associated with wave functions that represent the flaws.

17. The system of claim 16 wherein the generation device comprises a transducer.

18. The system of claim 16 wherein the detection device comprises an interferometer.

19. The system of claim 16 wherein the detection device comprises a gas coupled laser detection system.

20. The system of claim 16 wherein the detection device comprises an EMAT system.

21. The system of claim 16, wherein the material comprises a composite material.

22. The system of claim 16, wherein the wave function representing a flaw has:

an amplitude corresponding to a size of the flaw; and a basis function corresponding to a type of the flaw.

23. The system of claim 16, further comprising a graphical user interface to present a flaw.

24. The system of claim 23, wherein the representation is a B-scan image.

25. The system of claim 23, wherein the representation is a C-scan image.

* * * * *